May 22, 1973 V. P. QUINN Plant Pat. 3,341
CARNATION PLANT
Filed June 21, 1971
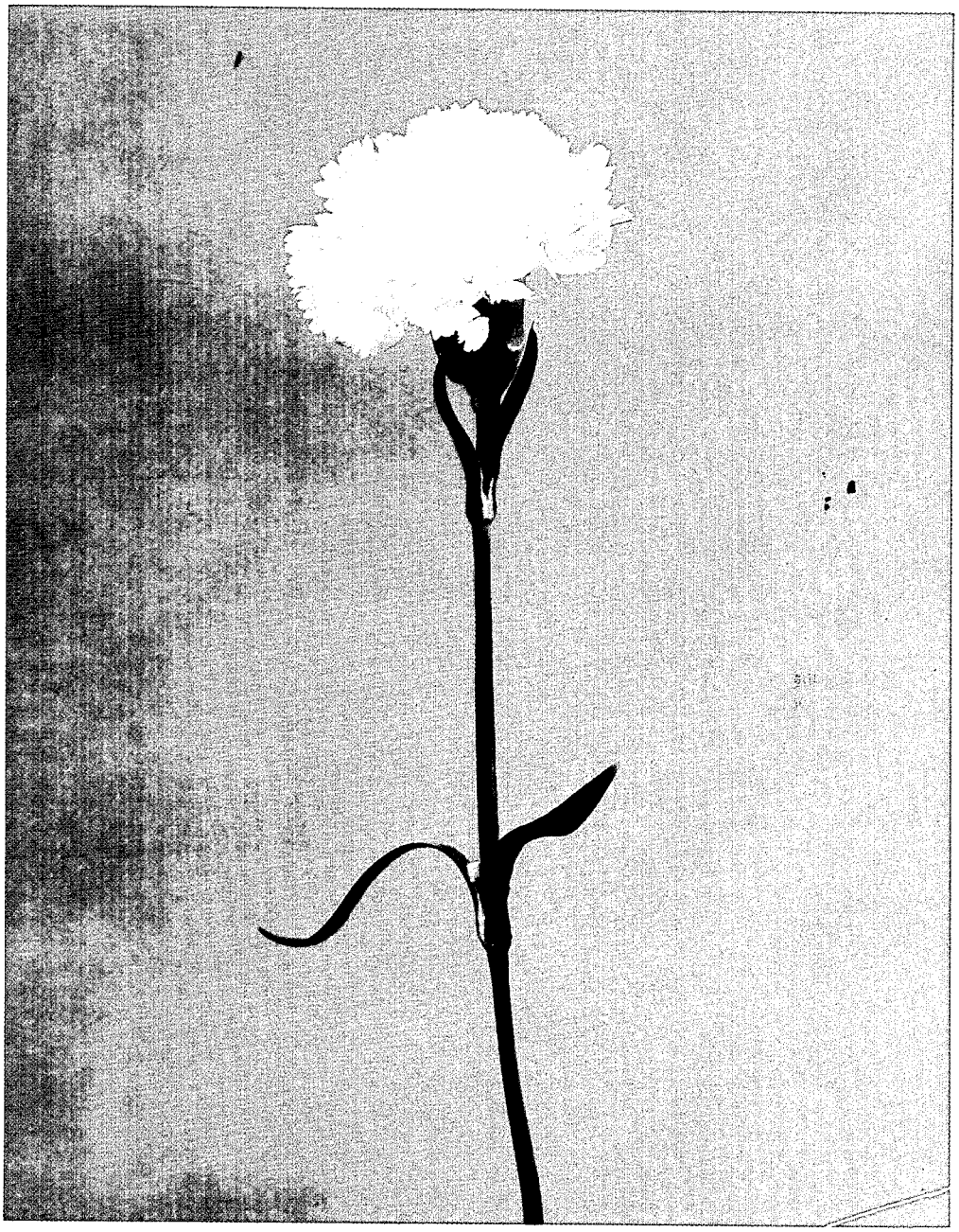

United States Patent Office

Plant Pat. 3,341
Patented May 22, 1973

3,341
CARNATION PLANT

Vincent P. Quinn, 1235 S. Irving St.,
Denver, Colo. 80219

Filed June 21, 1971, Ser. No. 155,365
Int. Cl. A01h 5/00
U.S. Cl. Plt.—70 1 Claim This invention relates to improvements in carnations, and the object of the invention is to provide a new and distinct variety of carnation plant in which the blossom is of a distinctive color and the growth is greatly improved.

This new variety, identified as "Quinn's Yellow," is a diploid sport from the "Tangerine" of Plant Patent No. 1,734, but has a bloom of a different color and has better growth habits than "Tangerine." Thus, the new variety has more vigorous growth, flowers faster, has stronger stems and has a better root system.

Asexual reproduction of this new variety was made at Denver, Colo., by taking cuttings and growing and selecting them in 1967, 1968, 1969 and 1970. The selected cuttings having consistently produced blossoms having the distinctive color hereinafter described in more detail.

The accompanying illustration is a color photograph of this new variety.

Following is a detailed description of the flower and plant of this new variety. Plate references are to the Dictionary of Color, Maerz and Paul, Second Edition, McGraw-Hill (1950).

*The plant*

Growth: Exceptionally vigorous and upright. Can withstand vigorous watering.

Flowering habit: Very productive of good blooms. Can be forced for all flowering.

Stems: Very strong and upright. Internodes 3½ to 4 inches long.

*Nodes.*—Large.

*Color.*—Chrome green, deep but with gray overlay to give bluish green color. (Plate 24, Column J. row 12.)

Foliage:

*Size.*—Average 4 inches long and ⅜ to ½ inch broad.

*Habit.*—Bottom foliage curls, top foliage straight.

*Color.*—Leaves same as stem.

*Quantity.*—Average.

Flower:

*Size.*—Large, averaging about 4 inches in diameter under normal greenhouse culture.

*Color.*—Between oyster white and sulfury citrus (Plate 10, row 6, columns G, H, I or J). This color does not change during the lifetime of the flower.

*Form.*—Full petaled, high centered and regular, with outer edge almost an unbroken circle.

*Calyx.*—Approximately parrot green (Plate 21, Row 6, column K). Very strong, tough and non-splitting.

*Longevity.*—Longer lasting than "Tangerine." Average picking quality.

*Fragrance.*—Mild and pleasant.

*Petals.*—Slightly fringed but not deeply cut. Guard petals are 1 to 1½ inches in width and spread to form a generally circular plane. Other petals are folded and tightly bunched together so that separate petals are not distinguishable.

Reproductive organs:

*Ovary.*—Large; high; pithy.

*Pistils.*—Small; curved but not curled; from ¾ to 1½ inches long; usually divided into two or three branches; seldom long enough to be visible in the open flower.

*Stamens.*—White; few; without anthers.

Having thus disclosed this discovery of a new variety of asexually reproduced plant, I claim:

1. The new and distinct variety of carnation plant, substantially as herein described and illustrated.

No references cited.

ROBERT E. BAGWILL, Primary Examiner